US012605095B2

(12) United States Patent
Price et al.

(10) Patent No.: US 12,605,095 B2
(45) Date of Patent: Apr. 21, 2026

(54) BLOOD COLLECTION ASSEMBLY

(71) Applicant: The Monarch Company, LLC, Birmingham, AL (US)

(72) Inventors: James Price, Birmingham, AL (US); Jonathan Trawick, Birmingham, AL (US); Clint Semmann, Waseca, MN (US)

(73) Assignee: The Monarch Company, LLC, Birmingham, AL (US)

( * ) Notice: Subject to any disclaimer, the term of this patent is extended or adjusted under 35 U.S.C. 154(b) by 193 days.

(21) Appl. No.: 18/062,432

(22) Filed: Dec. 6, 2022

(65) Prior Publication Data

US 2024/0180464 A1    Jun. 6, 2024

Related U.S. Application Data

(63) Continuation of application No. 16/390,499, filed on Apr. 22, 2019, now Pat. No. 11,529,080.

(51) Int. Cl.
| | |
|---|---|
| *A61B 5/15* | (2006.01) |
| *A61B 5/153* | (2006.01) |
| *A61M 25/00* | (2006.01) |
| *A61M 25/06* | (2006.01) |

(52) U.S. Cl.
CPC .... *A61B 5/150641* (2013.01); *A61B 5/15003* (2013.01); *A61B 5/150389* (2013.01); *A61B 5/150633* (2013.01); *A61B 5/15074* (2013.01); *A61B 5/150992* (2013.01); *A61B 5/153* (2013.01); *A61M 25/0097* (2013.01); *A61M 25/0631* (2013.01); *A61M 25/0637* (2013.01)

(58) Field of Classification Search
None
See application file for complete search history.

(56) References Cited

U.S. PATENT DOCUMENTS

| | | | |
|---|---|---|---|
| 3,734,080 | A | 5/1973 | Petterson et al. |
| 4,676,783 | A | 6/1987 | Jagger et al. |
| 4,747,831 | A | 5/1988 | Kulli |
| 4,781,692 | A | 11/1988 | Jagger et al. |
| 5,085,639 | A | 2/1992 | Ryan |
| 5,088,982 | A | 2/1992 | Ryan |
| 5,120,320 | A | 6/1992 | Fayngold |
| 5,176,655 | A | 1/1993 | McCormick et al. |

(Continued)

FOREIGN PATENT DOCUMENTS

| | | |
|---|---|---|
| CA | 2356199 | 6/2000 |
| CA | 2384546 | 4/2001 |

(Continued)

*Primary Examiner* — Jennifer Robertson
*Assistant Examiner* — Om Patel
(74) *Attorney, Agent, or Firm* — Todd R. Fronek; Larkin Hoffman Daly & Lindgren, Ltd.

(57) ABSTRACT

The present disclosure is a blood collection assembly that has a needle assembly fixedly coupled to a finger-activated actuator and tubing and the needle assembly has a needle. Further, the blood collection assembly has a hub that houses the needle assembly and the hub has a channel in a top surface of the hub. Additionally, the channel slidably engages the finger-activated actuator such that when the finger-activated actuator is moved from a distal end of the hub to a proximal end of the hub the needle retracts within the hub.

11 Claims, 4 Drawing Sheets

(56) References Cited

U.S. PATENT DOCUMENTS

| | | | |
|---|---|---|---|
| 5,498,241 A | 3/1996 | Fabozzi | |
| 5,501,674 A | 3/1996 | Trombley, III et al. | |
| 5,549,571 A | 8/1996 | Sak | |
| 5,573,512 A | 11/1996 | van den Haak | |
| 5,746,215 A | 5/1998 | Manjarrez | |
| 5,779,679 A | 7/1998 | Shaw | |
| 5,928,199 A | 7/1999 | Nakagami | |
| 5,951,525 A | 9/1999 | Thorne et al. | |
| 6,210,371 B1 | 4/2001 | Shaw | |
| 6,302,868 B1 | 10/2001 | Mohammad | |
| 6,309,376 B1 | 10/2001 | Alesi | |
| 6,616,630 B1 | 9/2003 | Woehr et al. | |
| 6,673,047 B2 | 1/2004 | Crawford et al. | |
| 6,743,186 B2 | 6/2004 | Crawford et al. | |
| 6,773,419 B2 | 8/2004 | Crawford et al. | |
| 6,835,190 B2 * | 12/2004 | Nguyen | A61M 25/0637 604/110 |
| 6,918,891 B2 | 7/2005 | Bressler et al. | |
| 7,018,344 B2 | 3/2006 | Bressler et al. | |
| 7,144,387 B2 | 12/2006 | Millerd | |
| 8,308,691 B2 | 11/2012 | Woehr et al. | |
| 8,469,927 B2 | 6/2013 | Shaw et al. | |
| D751,691 S | 3/2016 | Shaw | |
| 2002/0103464 A1 | 8/2002 | Crawford et al. | |
| 2003/0181874 A1 | 9/2003 | Bressler et al. | |
| 2004/0143195 A1 | 7/2004 | Bressler et al. | |
| 2005/0015055 A1 * | 1/2005 | Yang | A61B 5/150694 604/199 |
| 2005/0119627 A1 | 6/2005 | Crawford | |
| 2006/0100575 A1 | 5/2006 | Restelli et al. | |
| 2008/0108944 A1 | 5/2008 | Woehr et al. | |
| 2008/0171986 A1 | 7/2008 | Baid | |
| 2009/0292249 A1 * | 11/2009 | Moberg | A61M 5/158 604/164.08 |
| 2013/0116598 A1 | 5/2013 | Howell et al. | |
| 2013/0289524 A1 * | 10/2013 | Crawford | A61M 5/3204 604/506 |
| 2013/0296805 A1 | 11/2013 | Erskine | |
| 2016/0158504 A1 * | 6/2016 | Balboni | A61M 25/0631 604/263 |
| 2018/0271425 A1 * | 9/2018 | Rogers | A61B 5/150732 |
| 2019/0090798 A1 | 3/2019 | Shaw et al. | |
| 2020/0033001 A1 | 1/2020 | Feuerer | |

FOREIGN PATENT DOCUMENTS

| | | | | |
|---|---|---|---|---|
| CN | 1515329 | 7/2004 | | |
| EP | 3024514 | 6/2017 | | |
| JP | 2005-530540 A | 10/2005 | | |
| WO | WO-2005046750 A2 * | 5/2005 | | A61M 25/0612 |
| WO | WO-2007133951 A2 * | 11/2007 | | A61B 5/1405 |

* cited by examiner

BLOOD COLLECTION ASSEMBLY

BACKGROUND

Blood collection assemblies often comprise a small diameter needle having a pointed distal end and a proximal end mounted to a hub. Sometimes, the hub has wings mounted on either side. These wings may be used for a number of things. As an example, the wings may stabilize the blood collection assembly as the needle is inserted into a patient's arm.

Some blood collection assemblies have safety devices that protect users and patients from the needle after the needle has been used. For example, one blood collection assembly comprises a button that when selected actuates a spring drawing the needle into the hub. Another blood collection assembly comprises actuating wings, such that when the wings are rotated upward and together, a spring is initiated that retracts the needle. There are other types of safety devices on other blood collection assemblies.

Many of the existing safety devices are not put in place until the needle is removed from the person's arm. Thus, many existing safety devices still leave the needle exposed momentarily. This momentary exposure can lead to an accidental needle stick.

BRIEF DESCRIPTION OF THE DRAWINGS

The present disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure describes an exemplary blood collection assembly. The exemplary blood collection assembly comprises a hub that contains a needle assembly. In one embodiment, the hub comprises a set of wings that are used to balance the blood collection assembly as a needle is injected into a patient's arm.

Within a top side of the hub is a channel. Slidably coupled to the channel is a finger-activated actuator. The finger-activated actuator is situated toward the distal end of the hub when the needle is in an advanced position, such as when the needle is inserted into the patient's arm. When it is time to remove the needle from the patient's arm, a user slides the finger-activated actuator toward the proximal end of the hub until the needle is completely within the hub. Thus, the needle is removed from the patient's arm with little risk of accidental sticks.

In addition, at the distal end of the hub situated above the needle when the needle is in the advanced position is a compressed cotton and plastic shield. The compressed cotton and plastic shield is inside a compartment that is situated on a top side of the hub. When the needle is retracted by the finger-activated actuator, the compressed cotton and plastic shield falls down between the distal end of the needle and the needle opening in the hub. The cotton absorbs any excess liquid or blood and the plastic protects users from the distal end of the needle ensuring that the needle does not advance.

Figure 1:
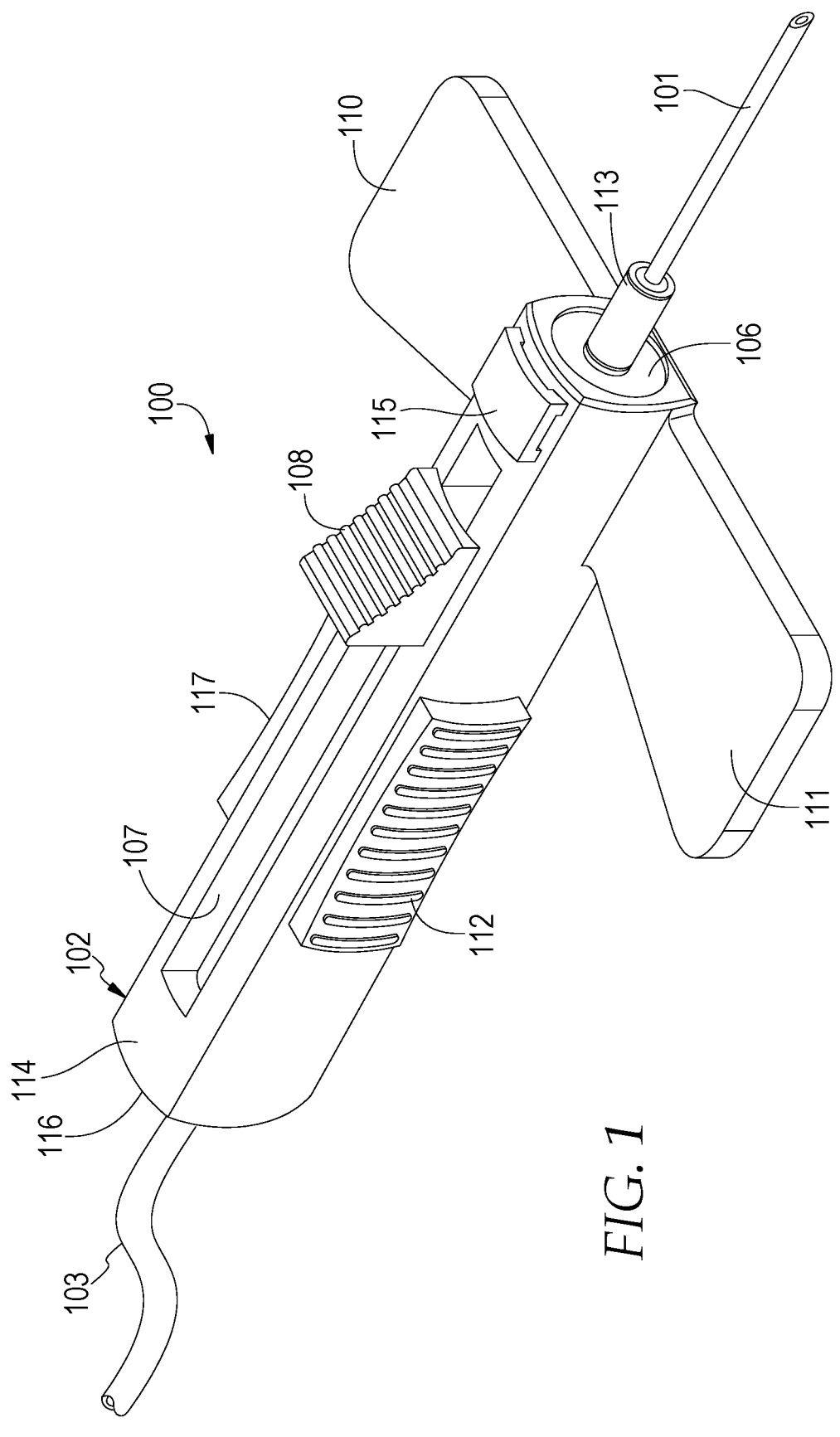
FIG. 1 is a perspective view of an exemplary blood collection assembly in accordance with an embodiment of the present disclosure with a needle advanced.

FIG. 1 is a perspective view of a blood collection assembly 100 in accordance with an embodiment of the present disclosure when a needle 101 is in an advanced position. An "advanced position" indicates that the needle is protruding for insertion into a patient's arm (not shown). The needle 101 protrudes from a plastic lid receptacle 113 to which a safety plastic lid (not shown) is coupled before use of the blood collection assembly 100.

The blood collection assembly 100 comprises a hub 102, a needle 101, and flexible tubing 103. In one embodiment, the flexible tubing 103 may comprise a clamp (not shown) for clamping the flexible tubing 103 to prohibit blood from fluidically travelling through the tubing. In use, the needle 101 is inserted in the patient's arm, blood flows through a needle assembly (not shown) that is coupled to the flexible tubing 103, and the blood flows through the flexible tubing 103 to a reservoir (not shown).

The blood collection assembly 100 further comprises a substantially cuboidal-shaped channel 107 formed in a top surface 114 of the hub 102. The substantially cuboidal-shaped channel 107 runs rectilinearly from a distal end 106 to a proximal end 116 of the hub 102. Slidably engaged with the cuboidal-shaped channel 107 is a finger-activated actuator 108, and the finger-activated actuator 108 is fixedly coupled to the needle assembly within the hub 102, which is described further herein.

In operation, a user inserts the needle 101 in a patient's arm. Blood is collected via the flexible tubing 103 in the reservoir. After the blood is collected, the user places his/her finger on the finger-activated actuator 108 and pulls the finger-activated actuator 108 to the proximal end 116 of the hub 102. Once the finger-activated actuator 108 has been moved to the proximal end 116 of the hub 102, the needle 101 is completely inside the hub 102. Thus, the needle 101 does not pose an accidental stick risk.

The blood collection assembly 100 further comprises wings 110 and 111. The wings 110 and 111 are coupled to and extend laterally from the distal end 106 of the hub 102. The wings 110 and 111 stabilize the blood collection assembly 100 while the needle 101 is inserted into the patient's arm. Further, the wings 110 and 111 stabilize the blood collection assembly 100 post insertion while blood is being drawn. Additionally, the wings 110 and 111 stabilize the assembly 100 when the finger-activated actuator 108 is actuated.

The blood collection assembly 100 further comprises a compartment 115. The compartment 115 houses a compressed cotton and plastic shield (not shown) that is housed in the hub 102. While the needle 101 is in the advanced position, the compressed cotton and plastic shield rests above the needle 101. However, when the needle 101 is moved to a retracted position via the finger-activated actuator 108, the compressed cotton and plastic shield falls between the distal end of the needle 101 and the plastic lid receptacle 113 inside the hub 102. The compressed cotton absorbs any fluid or blood that might leak from the needle 101 and the plastic shields the needle 101 from advancing through the plastic lid receptacle 113.

The blood collection assembly 100 further comprises gripper pads 112 and 117. The gripper pads 112 and 117 are coupled to or integral with the sides of the hub 102. The gripper pads 112 and 117 enable the user to easily grip the blood collection assembly 100 while in use. In this regard, the gripper pads 112 and 117 allow the user to easily grasp the blood collection assembly 100 when the user is collecting blood from the patient's arm or when the user is actuating the finger-activated actuator 108 to retract the needle 101.

Figure 2:
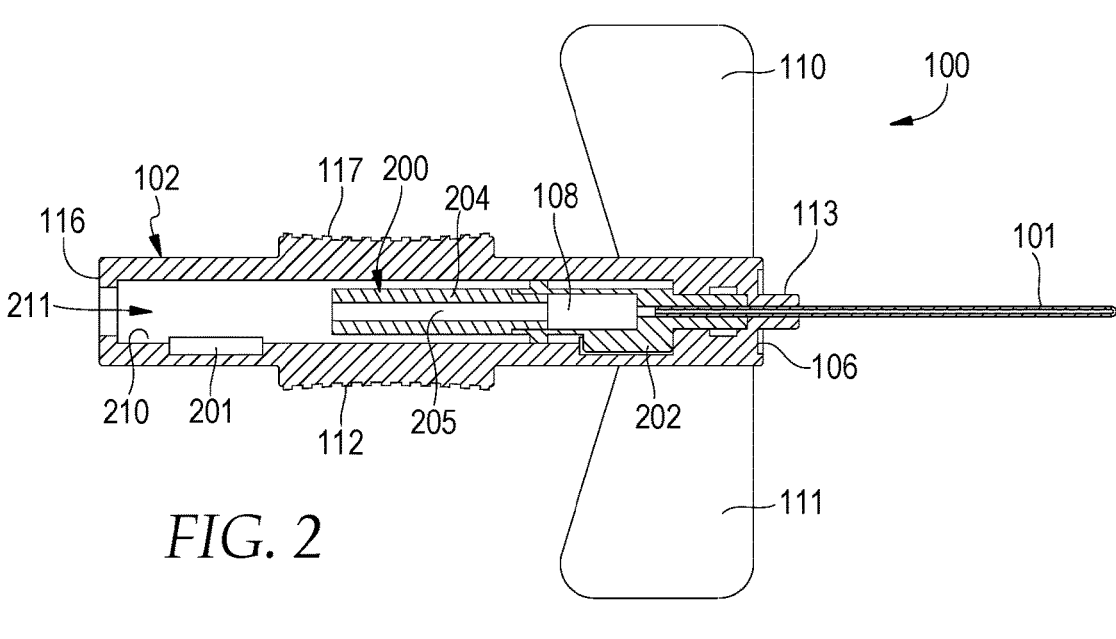
FIG. 2 is a top cross-sectional view of the blood collection assembly with the needle advanced as shown in FIG. 1.

FIG. 2 is a top cross-sectional view of the blood collection assembly 100 when the needle 101 is in the advanced position for insertion into a patient's arm. Note that prior to use of the blood collection assembly 100, a plastic lid (not shown) is coupled to the plastic lid receptacle 113 on the distal end of the hub 102 to protect from accidental sticks. In FIG. 2, the plastic lid is shown removed from the blood collection assembly 100, and the needle is exposed.

Note that the gripper pads 112 and 117 are shown coupled to or integral with the sides of the hub 102. As described hereinabove, the gripper pads 112 and 117 enable the user to easily grip the blood collection assembly 100 while in use.

Further note that the wings 110 and 111 are shown coupled to the distal end 106 of the hub 102. As described hereinabove, the wings 110 and 111 stabilize the blood collection assembly 100 while in use.

The blood collection assembly 100 further comprises a needle assembly 200. The needle assembly is moveably contained within a chamber 211 of the hub 102. The needle assembly 200 comprises a tubular member 204. The tubular member 204 comprises a cylindrical channel 204 defined by an inner wall 205. The needle assembly 200 is fixedly coupled to the needle 101 and the tubing 103 (FIG. 1). Additionally, the finger-activated actuator 108 is fixedly coupled to the needle assembly 200 such that when the finger-activated actuator 108 is moved from the distal end 106 to the proximal end 116 of the hub 102, the needle assembly 200 moves with the finger-activated actuator 108 from the distal end 106 to the proximal end 116 of the hub 102.

The needle assembly 200 further comprises a substantially rectangular-shaped protrusion 202. In operation, when the needle assembly 200 is moved via the finger-activated actuator 108 to the proximal end 116 of the hub 102, the rectangular-shaped protrusion 202 rests within a substantially rectangular-shaped indentation 201 in an inside surface 210 of the hub 102. In this regard, the rectangular-shaped protrusion 202 locks into the rectangular-shaped indentation 201 thereby fixing the needle assembly 200 at the proximal end of the hub 102. Thus, the needle assembly 200, including the needle 101, can no longer move toward the distal end 106 of the hub 102. Therefore, users are protected from the needle 101 when the needle assembly 200 is the retracted position, which is shown with reference to FIG. 6.

Figure 3:
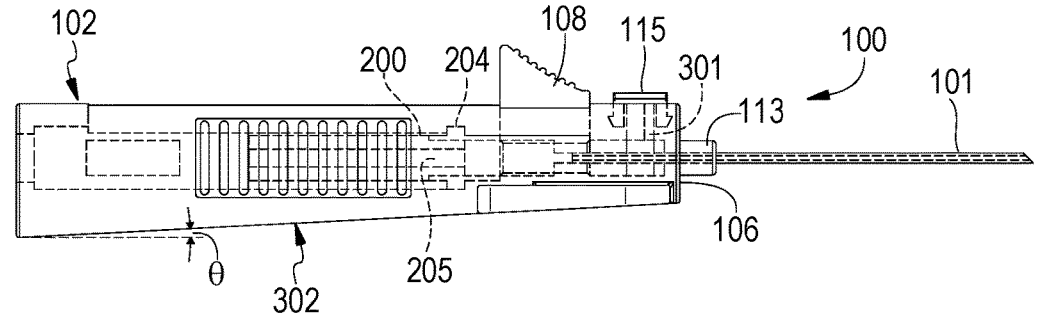
FIG. 3 is a side elevational view of the blood collection assembly with the needle advanced as shown in FIG. 1.

FIG. 3 is a side elevational view of the blood collection assembly 100 when the needle is in the advanced position. In this regard, the needle assembly 200 comprises the tubular member 204. The tubular member 204 comprises the cylindrical channel 204 defined by the inner wall 205. The needle assembly 200 comprises the needle 101 that is fixedly coupled to the tubular member 204. Additionally, the finger-activated actuator 108 is fixedly coupled to the needle assembly 200 such that when the finger-activated actuator 108 is moved from the distal end 106 to the proximal end 116 of the hub 102, the needle assembly 200 moves with the finger-activated actuator 108 to the proximal end 116 of the hub 102.

The blood collection assembly 100 further comprises a compressed cotton and plastic shield 301. The compressed cotton and plastic shield 301 is situated in the compartment 115 above the needle assembly 200 when the needle assembly 200 is in the advanced position. Note that as will be shown further herein, when the needle assembly 200 is retracted by the finger-activated actuator 108, the compressed cotton and plastic shield 301 falls downward resting between the distal end of the needle 101 and the receptacle 113. The compressed cotton of the shield 301 absorbs any excess liquid or blood from the needle 101, and the plastic portion of the shield 301 safely ensures that the needle 101 does not advance outwardly through the receptacle 113.

The blood collection assembly 100 further comprises an angled bottom surface 302. In one embodiment, the surface 302 is angled at an acute angle θ. When the blood collection assembly 100 is in use, the angled bottom surface 302 rests on the patient's arm thereby allowing the needle 101 to be more easily inserted. Further, the angle bottom surface 302 levels the blood collection assembly 100 so that when the finger-activated actuator 108 is moved by the user, the blood collection assembly 100 remains stabilized.

Figure 4:
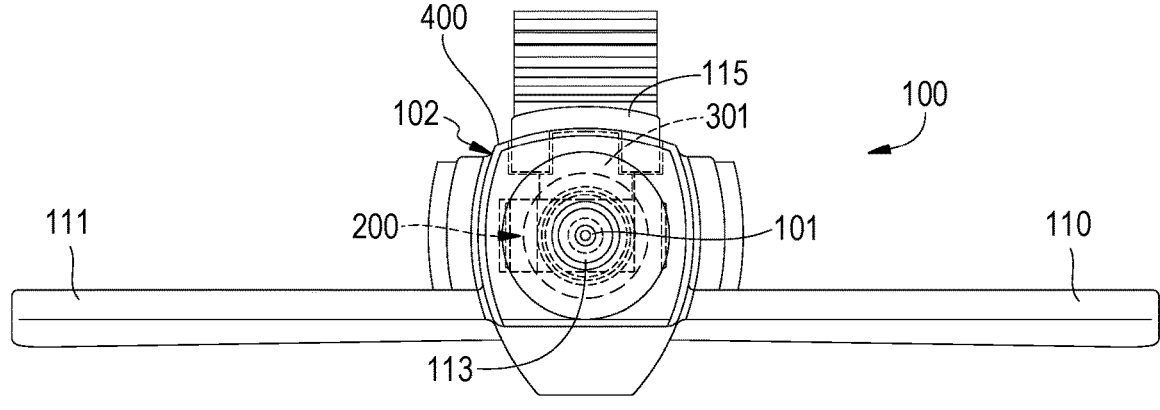
FIG. 4 is an end elevational view of the blood collection assembly with the needle advanced as shown in FIG. 1.

FIG. 4 is an end elevational view of the blood collection assembly 100 when the needle assembly 200 is in the advanced position and the needle 101 protrudes from the receptacle 113. Further, wings 110 and 111 protrude laterally from the hub 102 for stabilization of the blood collection assembly 100.

The blood collection assembly 100 comprises the compartment 115 that protrudes from an upper surface 400 of the hub 102. While the needle assembly 200 is in the advanced position, the compressed cotton and plastic shield 301 is situated within the compartment 115 above the needle 101. As will be shown further herein, when the needle assembly 200 is retracted, the compressed cotton and plastic shield 301 falls downward and rests between the distal end of the needle 101 and the receptacle 113.

Figure 5:
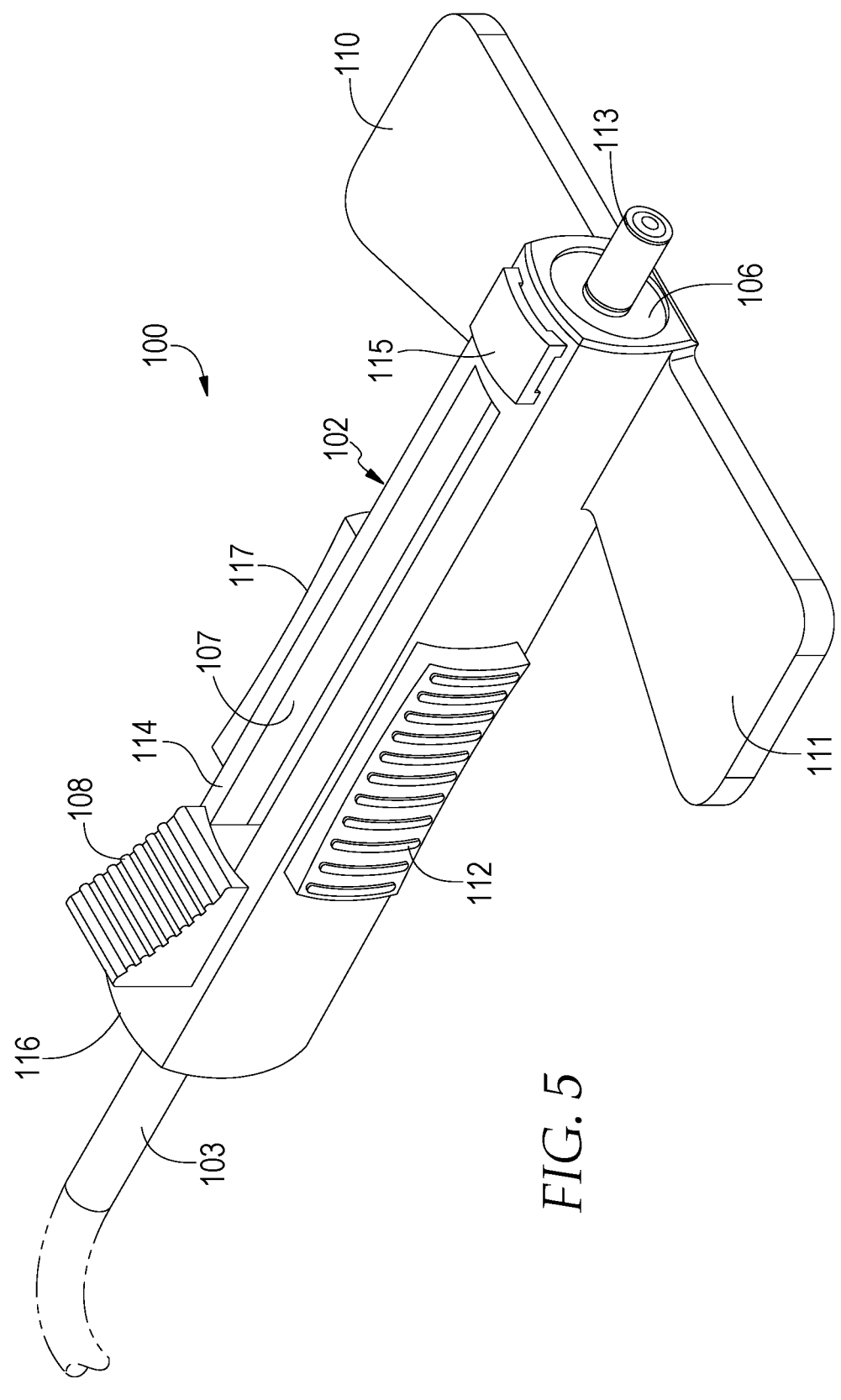
FIG. 5 is a perspective view of the blood collection assembly of FIG. 1 with the needle retracted.

FIG. 5 is a perspective view of the blood collection assembly 100 in accordance with an embodiment of the present disclosure when the needle 101 is in a retracted position. A "retracted position" indicates that the needle has been moved from the patient's arm and is housed within the hub 102. In this regard, the needle 101 no longer protrudes from the plastic lid receptacle 113.

As described hereinabove, the blood collection assembly 100 further comprises the substantially cuboidal-shaped channel 107 formed in the top surface 114 of the hub 102. The substantially cuboidal-shaped channel 107 runs rectilinearly from the distal end 106 to a proximal end 116 of the hub 102. Slidably engaged with the cuboidal-shaped channel 107 is the finger-activated actuator 108, and the finger-activated actuator 108 is fixedly coupled to the needle assembly 200 (FIG. 2) within the hub 102.

In operation, a user inserts the needle 101 in a patient's arm. Blood is collected via the flexible tubing 103 in the reservoir. After the blood is collected, the user places his/her finger on the finger-activated actuator 108 and pulls the finger-activated actuator 108 to the proximal end 116 of the hub 102. Once the finger-activated actuator 108 has been moved to the proximal end 116 of the hub 102, the needle

101 is completely inside the hub 102. Thus, the needle 101 no longer poses an accidental stick risk.

The blood collection assembly 100 further comprises the wings 110 and 111. As described hereinabove, the wings 110 and 111 are coupled to and extend laterally from the distal end 106 of the hub 102. The wings 110 and 111 stabilize the blood collection assembly 100 while the needle 101 is inserted into the patient's arm. Further, the wings 110 and 111 stabilize the blood collection assembly 100 post insertion while blood is being drawn.

The blood collection assembly 100 further comprises the compartment 115. The compartment 115 houses the compressed cotton and plastic shield 301 (FIG. 3) that is housed in the hub 102. While the needle 101 is in the advanced position, the compressed cotton and plastic shield 301 rests above the needle 101. However, when the needle 101 is moved to the retracted position via the finger-activated actuator 108, the compressed cotton and plastic shield 301 falls downwardly between the distal end of the needle 101 and the plastic lid receptacle 113 inside the hub 102. The compressed cotton absorbs any fluid or blood that might leak from the needle 101, and the plastic shields the needle 101 from advancing through the plastic lid receptacle 113.

As described hereinabove, the blood collection assembly 100 further comprises the gripper pads 112 and 117. The gripper pads 112 and 117 are coupled to or integral with the sides of the hub 102. The gripper pads 112 and 117 enable the user to easily grip the blood collection assembly 100 while in use.

Figure 6:
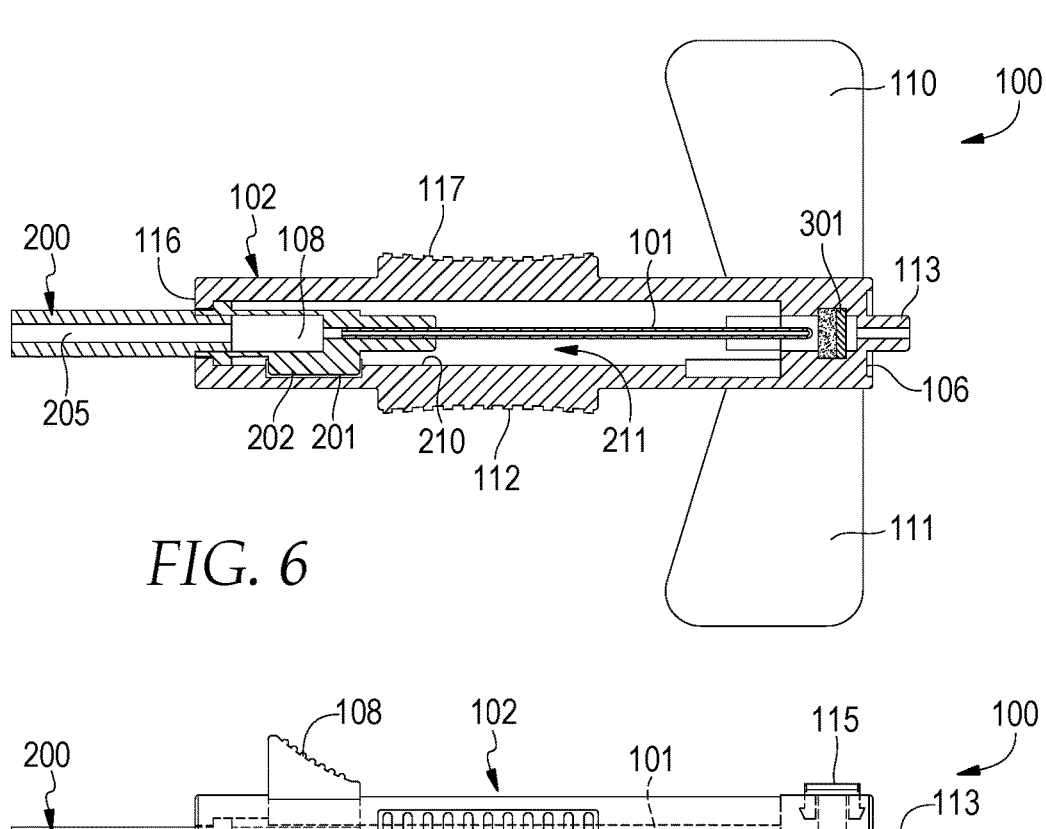
FIG. 6 is a top cross-sectional view of the blood collection assembly as shown in FIG. 1 with the needle retracted

FIG. 6 is a top cross-sectional view of the blood collection assembly 100 when the needle 101 is in the retracted position. Note that prior to use of the blood collection assembly 100, a plastic lid (not shown) is coupled to the plastic lid receptacle 113 on the distal end of the hub 102 to protect from accidental sticks. In FIG. 6, the plastic lid is shown removed from the blood collection assembly 100, and the needle is retracted.

Note that the gripper pads 112 and 117 are shown coupled to or integral with the sides of the hub 102. As described hereinabove, the gripper pads 112 and 117 enable the user to easily grip the blood collection assembly 100 while in use.

Further note that the wings 110 and 111 are shown coupled to the distal end 106 of the hub 102. As described hereinabove, the wings 110 and 111 stabilize the blood collection assembly 100 while in use.

The blood collection assembly 100 further comprises the needle assembly 200. The needle assembly 200 is moveably contained within the chamber 211 of the hub 102. The needle assembly 200 comprises the tubular member 204. The tubular member 204 comprises the cylindrical channel 204 defined by the inner wall 205. The needle assembly 200 is fixedly coupled to the needle 101 and the tubing 103 (FIG. 5). Additionally, the finger-activated actuator 108 is fixedly coupled to the needle assembly 200 such that when the finger-activated actuator 108 is moved from the distal end 106 to the proximal end 116 of the hub 102, the needle assembly 200 moves with the finger-activated actuator 108.

The needle assembly 200 further comprises the substantially rectangular-shaped protrusion 202. In operation, when the needle assembly 200 is moved via the finger-activated actuator 108 to the proximal end of the hub 102, the rectangular-shaped protrusion 202 rests within the substantially rectangular-shaped indentation 201 within an inside surface 210 of the hub 102. In this regard, the rectangular-shaped protrusion 202 locks into the rectangular-shaped indentation 201 thereby fixing the needle assembly 200 at the proximal end of the hub 102. Thus, the needle assembly

200, including the needle 101, can no longer move toward the distal end 106 of the hub 102. Therefore, users are protected from the needle 101 when the needle assembly 200 is in the retracted position.

Further, when the needle assembly 200 is moved to the proximal end 116 of the hub 102, the compressed cotton and plastic shield 301 falls downwardly. The compressed cotton and plastic shield 301 rests between the distal end of the needle 101 and the receptacle 113. Thus, the compressed cotton portion of the shield absorbs any fluid or blood that escapes the needle 101. The plastic portion of the shield 301 safely ensures that the needle 101 does not advance outwardly through the receptacle 113 posing an accidental stick risk.

Figure 7:
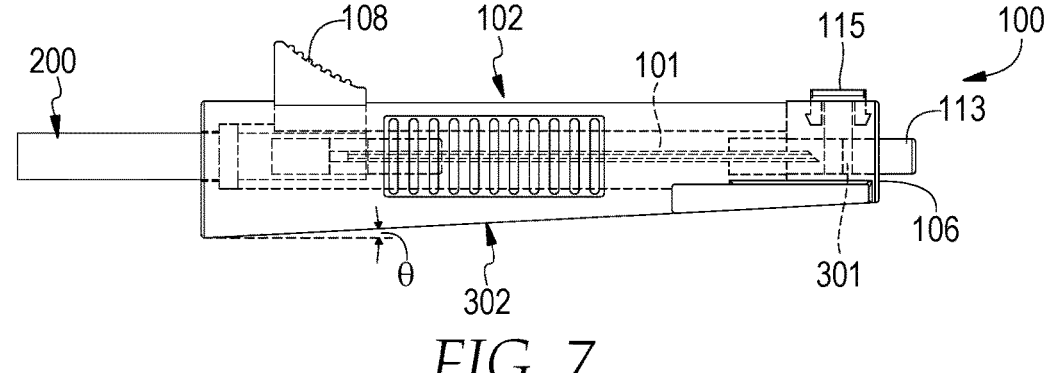
FIG. 7 is a side elevational view of the blood collection assembly as shown in FIG. 1 with the needle retracted.

FIG. 7 is a side elevational view of the blood collection assembly 100 when the needle is in the retracted position. In this regard, the needle assembly 200 comprises the needle 101. Additionally, the finger-activated actuator 108 is fixedly coupled to the needle assembly 200 such that when the finger-activated actuator 108 is moved from the distal end 106 to the proximal end 116 of the hub 102, the needle assembly 200 moves with the finger-activated actuator 108.

The blood collection assembly 100 further comprises the compressed cotton and plastic shield 301. When in the retracted position, the compressed cotton and plastic shield 301 is situated between the distal end of the needle 101 and the receptacle 113. The compressed cotton of the shield 301 absorbs any excess liquid or blood from the needle 101, and the plastic portion of the shield 301 safely ensures that the needle 101 does not advance outwardly through the receptacle 113.

The blood collection assembly 100 further comprises the angled bottom surface 302. In one embodiment, the surface 302 is angled at an acute angle $\theta$. When the blood collection assembly 100 is in use, the angled bottom surface 302 rests on the patient's arm thereby allowing the needle 101 to be more easily inserted. Further, the angle bottom surface 302 levels the blood collection assembly 100 so that when the finger-activated actuator 108 is moved by the user, the blood collection assembly 100 remains stabilized.

Figure 8:
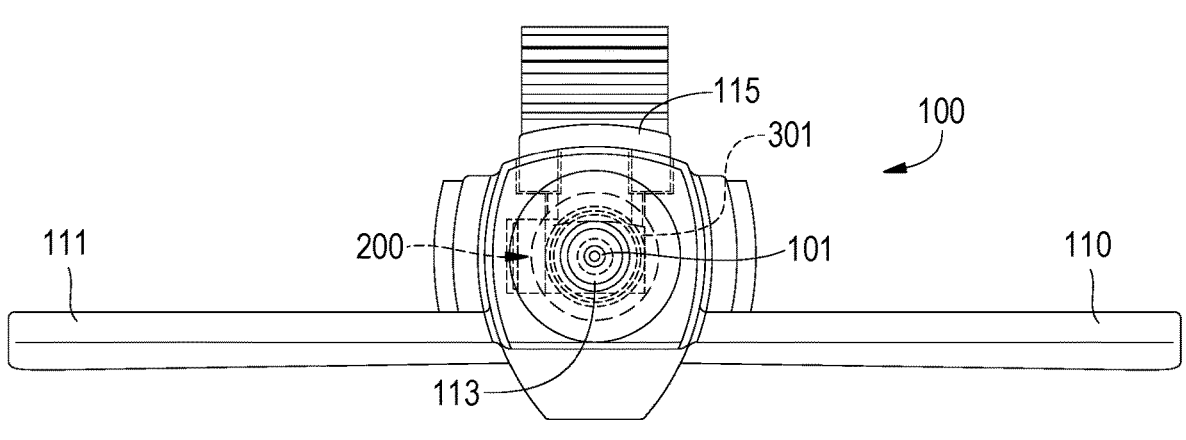
FIG. 8 is an end elevational view of the blood collection assembly as shown in FIG. 1 with the needle retracted.

FIG. 8 is an end elevational view of the blood collection assembly 100 when the needle assembly 200 is in the retracted position and the needle 101 (FIG. 6) is within the hub 102.

The blood collection assembly 100 comprises the compartment 115 that protrudes from an upper surface 400 of the hub 102 and houses the compressed cotton and plastic shield 301. When the needle assembly 200 is moved to the retracted position, the compressed cotton and plastic shield 301 falls downward and rests between the distal end of the needle 101 and the receptacle 113.

The invention claimed is:

1. A blood collection assembly, comprising:
a hub comprising a proximal end, a distal end, a channel, a chamber and a compartment, the channel in communication with the chamber, the channel further extending along a top side of the hub, the channel terminating at a distal position on the top side of the hub, the channel and chamber extending in a longitudinal direction from the proximal end to the distal end of the hub, the compartment extending in an orthogonal direction to the longitudinal direction and positioned in a spaced-apart relationship from the distal position on the top side of the hub with the compartment positioned distal the channel;
a needle assembly having a needle and a finger-activated actuator, the needle assembly slidable along the channel in the longitudinal direction from an advanced position to a retracted position, wherein a distal tip of the needle is positioned distal the hub when the needle assembly is in the advanced position and the distal tip is positioned within the chamber of the hub when the needle assembly is in the retracted position; and a shield positioned within the compartment between a cover on the top side of the hub and a longitudinal extent of the needle when the needle assembly is in the advanced position, wherein when the needle assembly slides along the channel to the retracted position, the shield falls downward in the compartment to be positioned between the distal tip and the distal end of the hub.

2. The blood collection assembly of claim 1, wherein the hub further includes at least two wings projecting laterally from a bottom side of the hub.

3. The blood collection assembly of claim 1, wherein the shield is formed of compressed cotton and plastic.

4. The blood collection assembly of claim 1, further comprising flexible tubing connected to the needle assembly.

5. The blood collection assembly of claim 1, wherein in the advanced position, the shield rests above the needle.

6. The blood collection assembly of claim 1, wherein the needle assembly includes a protrusion and the hub includes an indentation on an inner surface of the hub, wherein the protrusion locks into the indentation when the needle assembly is in the retracted position.

7. The blood collection assembly of claim 1, wherein the hub defines a chamber and the needle assembly includes a tubular member positioned within the chamber, the finger-mactivated actuator positioned on a top surface of the hub and fixedly connected to the tubular member through the channel.

8. The blood collection assembly of claim 1, further comprising gripper pads positioned on opposite sides of the hub.

9. The blood collection assembly of claim 1, further comprising a lid receptacle positioned at a distal end of the hub and configured to receive a lid.

10. The blood collection assembly of claim 9, wherein the shield rests between the distal tip of the needle and the lid receptacle when the needle assembly is in the retracted position.

11. The blood collection assembly of claim 1, wherein the compartment protrudes from an upper surface of the hub.

* * * * *